United States Patent [19]

Mahant

[11] Patent Number: 5,624,813

[45] Date of Patent: Apr. 29, 1997

[54] NAD(P)⁺/NAD(P)H BASED CHEMILUMINESCENT DIAGNOSTICS

[76] Inventor: Vijay K. Mahant, 5669 Amaya Dr., #367, La Mesa, Calif. 91942

[21] Appl. No.: 230,848

[22] Filed: Apr. 21, 1994

[51] Int. Cl.⁶ ................................................. C12Q 1/28
[52] U.S. Cl. ..................................... 435/28; 424/94.1
[58] Field of Search ............................ 435/4, 25, 26, 435/28; 424/94.1, 94.2, 94.4

[56] References Cited

U.S. PATENT DOCUMENTS

| | | | |
|---|---|---|---|
| 3,875,011 | 4/1975 | Rubenstein et al. | 195/99 |
| 4,191,613 | 3/1980 | Ullman et al. | 435/188 |
| 4,234,681 | 11/1980 | DeLuca-McElroy | 435/8 |
| 4,246,340 | 1/1981 | Lundin et al. | 435/8 |
| 4,302,537 | 11/1981 | Gündermann et al. | 435/7 |
| 4,380,580 | 4/1983 | Boguslaski et al. | 435/7 |
| 4,581,335 | 4/1986 | Baldwin | 435/172.3 |
| 4,647,532 | 3/1987 | Watanabe et al. | 435/28 |
| 4,649,105 | 3/1987 | Kasahara et al. | 435/5 |
| 4,927,752 | 5/1990 | Remacle | 435/8 |
| 5,094,939 | 3/1992 | Okada et al. | 435/6 |
| 5,200,325 | 4/1993 | Blatt et al. | 435/14 |
| 5,202,091 | 4/1993 | Lisenbee | 422/52 |
| 5,202,234 | 4/1993 | Shah et al. | 435/7.4 |
| 5,250,415 | 10/1993 | Ebeling et al. | 435/14 |
| 5,250,416 | 10/1993 | Ohno et al. | 435/15 |
| 5,250,420 | 10/1993 | Asano et al. | 435/26 |
| 5,278,044 | 1/1994 | San George et al. | 435/26 |

FOREIGN PATENT DOCUMENTS

| | | |
|---|---|---|
| 0124909 | 11/1984 | European Pat. Off. . |
| 0285998 | 10/1988 | European Pat. Off. . |
| 9410337 | 5/1994 | WIPO . |

OTHER PUBLICATIONS

Tsuji et al (1989) J Bioluminescence and Chemilum. 4: 454–462.
Bauer et al. p. 496, in *Bray's Clin. Chem.*, Tietz, ed., Saunders, Philadelphia.
Sigma Diagnostics procedured for isocitrate dehydrogenase determination, citing *Bray's Clin. Chem.*, Tietz, ed., Saunders, Philadelphia.
WPI, Section Ch, Week 9003; Derwent Pubs. Ltd., London, GB; Class B04, An 90–018122 & JP, A, 01 296 999; Mitsubmishi Gas Chem KK; Nov. 30, 1989; (abstract provided).
WPI; Section Ch, Week 8820; Derwent Pubs. Ltd., London, GB; Class B01, AN 88–138063 & JP, A, 63 081 266; Fuji Photo Film KK; Apr. 12, 1988 (abstract provided).
WPI; Section Ch, Week 8803; Derwent Pubs. Ltd., London, GB; Class B04, AN 88–017466 & JP, A, 62 278 997; Iatron Laboratories; Dec. 3, 1989 (abstract provided).
Avigliano et al. (1985) "Oxidation of NAD dimers by horseradish peroxidase" *Biochem. J.* 226:391–395.
Kachmar et al. (1976), pp. 652–660 in *Enzymes, in Fundamentals of Clinical Chemistry*, Tietz, ed., Saunders, Philadelphia.
Pp. 28–30, in *Peroxidases in Chemistry and Biology*, vol. II, Everse et al., eds., CRC Press, Boston (1991).

Naruse et al. (1992) "A Method of PKU screening using phenylalanine dehydrogenase and microplate system" *Screening* 1:63–66.
Tsuji et al. (1989) "Chemiluminescent Enzyme Immunoassay A Review" *Analytical Sci.* 5:497–506.
Tsuji et al. (1990) "Enzyme Immunoassays Monitored by Chemiluminescence Reactions of Lucigenion and NADH" *Luminescence Immunoassay and Molecular Applications*, Chapter 10, pp. 157–172.
Tsuji et al. (1989) "Chemiluminescent Assay of Co–factors" *J. Bioluminescence and Chemiluminescence* 4:454–462.
Yokota et al. "Reaction of Peroxidase with Reduced Nicotinamide–Adenine Dinucleotide and Reduced Nicotinamide–Adenine Dinucleotide Phosphate" (1965) *Biochim. Biophys. Acta* 105:301–312.
Lunn et al. (1989) "Automated enzymatic assays for the determination of intestinal permeability probes in urine. 2. Mannitol" *Clinica Chimica Acta* 183:163–170.
Zimmerman et al. (1993), "Respiratory Burst of Blood Cells in Patients with Gastrointestinal Cancers", pp. 496–500, in *Proceedings of the VIIth Internatl. Symp. on Bioluminescence and Chemiluminescence*, Banff, Szalay et al., eds., John Wiley and Sons, Chichester.
Bierlich et al. (1993), "Chemiluminescence Response of Bone Marrow in Pediatric Patients with Acute or Chronic Leucemias", pp. 441–445, in *Proceedings of the VIIth Internatl. Symp. on Bioluminescence and Chemiluminescence*, Banff, Szalay et al., eds., John Wiley and Sons, Chichester.
Bronstein et al. (1989) "A Comparison of Chemiluminescent and Colorimetric Substrates in a Hepatitis B Virus DNA Hybridization Assay", *Anal. Biochem.* 180:95–98.
Wood (1989) "Routine Luminescence Immunoassays—Dream or Reality" *J. Bioluminescence and Chemiluminescence* 4:79–87.
Maeda et al. (1989) "Chemiluminescent Assay of Various Enzyme Activities and its Application to Enzyme Immunoassays" *J. Bioluminescence and Chemiluminescence* 4:140–148.

(List continued on next page.)

*Primary Examiner*—Carolyn Paden
*Attorney, Agent, or Firm*—Crockett & Fish

[57] ABSTRACT

Chemiluminescence-based assays that detect or quantify determine NAD(P)-linked dehydrogenases and oxidoreductases, or the cofactors, or detect or quantify substrates, intermediates or products of reactions catalyzed by these enzymes by coupling the enzyme reactions to luminescence generating systems. The assays include the steps of reacting a peroxidase with the NAD(P)H produced in a reaction catalyzed by an oxidoreductase that requires NAD(P)⁺/NAD(P)H as a cofactor; and then adding a chemiluminescent moiety to produce chemiluminescence from which the analyte, such as an amino acid or sugar, the activity of the oxidoreductase or NAD(P)⁺/NAD(P) analyte, is determined. The assays are particularly useful for determining amino acids and sugars and, thus, are useful for quantitating amino acids and sugars in foods and for screening tissues body fluids, particularly blood, for diagnosing and managing metabolic defects in neonates and in adults.

15 Claims, No Drawings

OTHER PUBLICATIONS

Cocco et al. (1988) "NADH–oxidase from the extreme thermophile *Thermus aquaticus* YT–1 Purification and Characterization" *Eur. J. Biochem.* 174(2):267–271.

Kuo et al. (1988) "Stimulation of the Activity of Horseradish Peroxidase by Nitrogenous Compounds" *J. Biol. Chem.* 263:3811–3817.

Lowe et al. (1972) "Microfluometry of Glucose–6–Phosphate Dehydrogenase and 6–Phosphogluconate Dehydrogenase in Red Cells" *Clin. Chem.* 18:440–445.

Bauer et al. (1970), pp. 449–453, in *Bray's Clin. Chem.*, Tietz, ed., Saunders, Philadelphia (as cited in the SIGMA Chemicals catalog).

Elliott et al. "'α–Hydroxybutyric Dehydrogenase' in Myocardial Infarction and in Liver Disease" *Lancet* Apr. 1, 1961.

NAD(P)⁺/NAD(P)H BASED CHEMILUMINESCENT DIAGNOSTICS

FIELD OF THE INVENTION

The present invention relates to chemiluminescence-based assays. The assays detect or quantify oxidoreductases, including dehydrogenases, that catalyze reactions in which NADH/NAD$^+$ or NADPH/NADP$^+$ are cofactors. In particular, the assays determine NAD(P)-linked dehydrogenases and oxidoreductases, or the cofactors, or detect or quantify substrates, intermediates or products of reactions catalyzed by these enzymes by coupling the enzyme reactions to luminescence generating systems. The assays are highly sensitive and are particularly useful, for example, for determining amine acids. The assays thus can be used to screening body fluids and tissues to detect analytes indicative of diseases, such as hypothyroidism, galactosemia, phenylketonuria (PKU), and maple syrup urine disease, and for testing foods to quantitate certain nutrients. The assays may also be used to quantify amine acids in foods. The assays provide multi-analyte detection methods that can be used to perform numerous assays on small amounts of sample and that can be readily automated.

BACKGROUND OF THE INVENTION

Luminescence-based Assays

Molecular luminescence is the emission of electromagnetic (EM) radiation, including ultraviolet (UV), visible and infrared (IR) light, from a molecule as it returns from an excited state to a lower energy state, usually the ground state of the molecule. Luminescence includes radioluminescence, chemiluminescence, which includes bioluminescence, and photoluminescence, which includes fluorescence and phosphorescence. Coupling of luminescent labels or reactions to assays, such as immuneassays, has provided convenient and sensitive assays. Chemiluminescence is produced when the excited product of an exoergic chemical process reverts to its ground state with the emission of light. Most chemiluminescent reactions require a step that involves oxidation of a reactant with molecular oxygen or its synthetic equivalent. Chemiluminescence is coupled to assays by using molecules, such as luminol, acridinium esters, isoluminol, lucigenin, dioxetanes and oxalate esters, that are capable of exhibiting chemiluminescence or transferring energy to an appropriate acceptor luminescent molecule or compound. The best known chemiluminescent reactions are those of the acridinium esters, of luminol and of lucigenin. In luminol, and isoluminol, chemiluminescent reactions, the key oxidative step involves reactions of hydrogen peroxide and aminophthalhydrazide in the presence of suitable catalysts.

Chemiluminescence is employed in several types of assays. It is employed in: (1) assays that use chemiluminescent labels, such as isoluminol derivatives or acridinium esters; (2) chemiluminescent assays that use agents, such as luminol, in combination with peroxide generating substrates, peroxidases and enzymes, such as oxidoreductases; (3) assays that involve electron transfer and fragmentation pathways that generate chemiluminescence; and (4) bioluminescence, which involves the use of biological substrates and enzymes, such as luciferin and luciferase, to generate light. Of particular interest herein, are chemiluminescent assays that are used to determine dehydrogenases and their cofactors NAD(P)/NAD(P)H.

Dehydrogenase Assays

The coenzymes nicotinamide adenine dinucleotide (NAD) and nicotinamide adenine dinucleotide phosphate (NADP) serve as transient intermediate carriers of hydride ions that are enzymatically removed from a molecule by the action of certain dehydrogenases and oxidoreductases (see, e.g., Table 1, below). Dehydrogenases are oxidoreductases that catalyze the removal of hydrogen atoms from molecules, such as glucose, and transfer them to NAD(P)$^+$, which carry electrons from such catabolic reactions to electron-requiring biosynthetic reactions. Most electron pairs that enter the respiratory chain are produced by the action of NAD(P)-linked dehydrogenases. NAD(P)-linked dehydrogenases participate in carbohydrate catabolism, the citric acid cycle, the fatty acid oxidation cycle. Thus, reactions involving dehydrogenases and oxidoreductases that catalyze the conversion of the substrate into product in the presence of the cofactor NAD(P)$^+$, which is reduced to NAD(P)H, occur in many metabolic pathways and biological reactions. Almost every substance of biological interest can be measured using NAD(P)H in the presence of an appropriate dehydrogenase.

Because of the importance of the enzymes, cofactors, reactants and products, numerous assays to determine dehydrogenases or substrates thereof have been developed. The assays currently practiced rely on the use of an electron carrier, such as 1-methoxyphenazinium methylsulfate (1-MPMS$^+$), which is reduced to 1-MPMSH$_2$ by NAD(P)H that is generated in the dehydrogenase reaction. In some assays, the reduced electron carrier is then used to reduce a compound, such as 3-(4,5-dimethylthiazol-2-yl)-2,5-diphenyltetrozolium bromide (MTT), to formazan dye (MTTH$_2$) and thereby produce a color change or produce fluorescence that can be detected spectrophotometrically or fluorophotometrically (see, e.g., U.S. Pat. No. 5,250,420; Naruse et al. (1992) Screening 1:63–66). Alternatively, the reduced electron carrier, such as 1-MPMSH$_2$, is used to generate superoxide anion (O$_2^-$), which dismutates to form hydrogen peroxide (H$_2$O$_2$). Generated O$_2^-$ and/or H$_2$O$_2$ are then reacted with a chromogen that develops a color or changes color or a fluorogen that produces a fluorescent product. The change in color can be detected colorimetrically and the fluorescence can be detected fluorometrically. Spectrophotometric methods have detection limits for NADH as low as about 10$^{-9}$ mol/assay and fluorometric methods have detection limits as low as about 10$^{-10}$ mol/assay (see, e.g., Tsuji et al. (1989) Analytical Sci. 5:497–506).

Since spectrophotometric methods are not sufficiently sensitive for many diagnostic needs, chemiluminescent methods, which have greater sensitivity, have been developed. In certain of these methods, O$_2^-$ and H$_2$O$_2$ are generated as described above and are reacted with a chemiluminescent moiety, such as luminol, in the presence of microperoxidase (mPOD) to generate light (see, e.g., U.S. Pat. No. 5,250,420; Tsuji et al. (1990) in Luminescence Immunoassay and Molecular Applications, pages 157–172; and Tsuji et al. (1989) J. Bioluminescence and Chemiluminescence 4:454–462).

Chemiluminescence-based Assays

The principle of the chemiluminescence-based assays that use NAD(P)H and dehydrogenases can be summarized as follows:

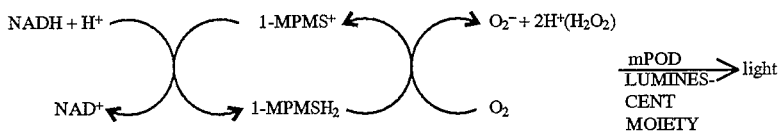

Assays that measure dehydrogenase or oxidoreductase activity, NAD(P)+, NAD(P)H, or substrates or products of reactions catalyzed by dehydrogenases or oxidoreductases in the presence of nicotinamide dinucleotides can be adapted to detect many substances of biological interest. Consequently, such assays are useful for diagnosis of diseases involving metabolic defects. Numerous diagnostic assays, particularly neonatal diagnostic assays, rely on the above-described reactions.

Diagnostic Assays for Inborn Errors of Metabolism and Acquired Metabolic Disorders A number of diseases are caused by or involve deficient or defective enzymes in intermediary metabolism (see, e.g., Tables 1 and 2, below) that result, upon ingestion of the enzyme substrates, in accumulation of harmful metabolites that damage organs and tissues, particularly an infant's developing brain and other organs, resulting in mental retardation and other developmental disorders. Management of the diet of the infant to avoid ingestion of such substrates or administration of appropriate medication can prevent or ameliorate the symptoms of the resulting disorders. The earlier such defects are diagnosed and management begins, the better the chance for prevention of the symptoms of the disorder. Thus, screening of neonates and infants for identification of those at risk for these disorders is of great importance in preventing mental retardation and other disabilities. Because of cost limitations and test availability and because such assays require blood samples, which can only be obtained in limited amounts from neonates, the number of diseases for which neonates and infants are screened is limited.

Thus, in order to effectively use the available diagnostics to detect inborn errors of metabolism and to improve diagnostic efficacy, reduce cost and reduce sample misidentification in such diagnostics, and to improve the ability to determine molecules of biological interest, there is a need to increase the sensitivity of such assays.

Therefore, it is an object herein to provide highly sensitive methods to quantify oxidoreductase activity in which NAD(P)+/NAD(P)H, NAD(P)+/NAD(P)H are co-factors, and to are co-factors. It is also an object herein to provide highly sensitive diagnostic assays for routine screening of neonates for detecting inborn errors of metabolism and of older subjects for diagnosing and managing acquired metabolic disorders.

SUMMARY OF THE INVENTION

Assays that detect or quantify oxidoreductases, including dehydrogenases, that catalyze reactions in which NADH/NAD+ or NADPH/NADP− are cofactors are provided. In particular, the assays determine NAD(P)-linked dehydrogenases and oxidoreductases and detect or quantify substrates, intermediates or products of reactions catalyzed by these enzymes or the cofactors by coupling the enzyme reactions to luminescence generating systems. The assays are highly sensitive and are useful, for example, for determining amino acids and sugars. The assays, thus, are used for screening body fluids and tissues, including serum, saliva, sweat, blood, hair and cerebral spinal fluid (CSF), for diagnosis and management of certain diseases, including congenital hypothyroidism, galactosemia, phenylketonuria (PKU) and maple syrup urine disease, and for assaying the amino acid or sugar content of foods or food additives. The assays are particularly useful for screening blood, particularly neonatal blood, for diagnosis of such diseases. The assays provide multi-analyte detection methods that can used to perform multi-analyte analysis on small amounts of sample and that can be readily automated.

The assays herein provide a substantial increase in stability of the reagents, enhanced convenience, and use less sample than prior assays involving dehydrogenases (see, e.g., U.S. Pat. No. 5,250,420) and prior assays for dehydrogenases that rely on chemiluminescence or bioluminescence (see, e.g., Tsuji et al. (1990) in *Luminescence Immunoassay and Molecular Applications*, eds. Van Dyke et al., CRC Press, Boca Raton, Fla., pages 157–172; and Tsuji et al. (1989) *J. Bioluminescence and Chemiluminescence* 4:454–462).

The assays provided herein are represented by the following scheme:

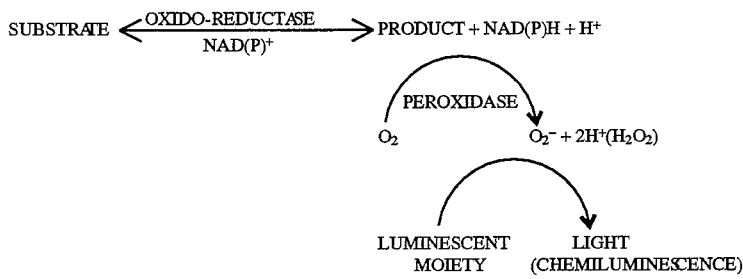

quantify or detect the substrates, products or intermediates of reactions catalyzed by dehydrogenases or oxidoreductases in which NAD(P)+/NAD(P)H, NAD(P)+/NAD(P)H These assays can be used to detect substrates of oxidoreductases or dehydrogenases or cofactors, intermediates or products of reactions catalyzed by such enzymes, the oxidoreductases or dehydrogenases, or NADH/NAD$^+$ or NADPH/NADP$^+$ or substrates, enzymes, cofactors and products that can be coupled to the reactions in the assays.

As discussed above, prior assays for dehydrogenases and NAD(P)$^+$/NAD(P)H rely on the use of an electron mediator, such as 1-methoxyphenazinium methylsulfate (1-MPMS$^+$), which is reduced by NADH to 1-MPMSH$_2$, which is then used to generate superoxide anion (O$_2^-$), which can dismutate to form hydrogen peroxide (H$_2$O$_2$). Generated O$_2^-$ (H$_2$O$_2$) react with a chemiluminescent moiety, such as luminol, in the presence of microperoxidase to generate light. These prior assays use an electron mediator because the aerobic oxidation of reduced nicotinamide nucleotides (NADH, NADPH) to produce superoxide anion (O$_2^-$) and hydrogen peroxide (H$_2$O$_2$) in the presence of peroxidase was thought to occur only at acidic pH (see. e.g., Yokota et al. (1965) *Biochim. Biophys. Acta* 105:301–312; Avigliano et al. (1985) *Biochem. J.* 226:391–395; see, also, page 29, in *Peroxidases in Chemistry and Biology*, Vol. II, Everse et al., eds, CRC Press, Boston (1991)).

In contrast, the methods provided herein do not rely on or require an electron mediator. Instead, a peroxidase, such as horseradish peroxidase, catalyzes the oxidation of reduced nicotinamide nucleotides (NADH, NADPH) and produces superoxide anion (O$_2^-$) and, by dismutation, hydrogen peroxide (H$_2$O$_2$). The peroxidase is then also used to catalyze the reaction between the O$_2^-$ and/or H$_2$O$_2$ with the luminescent moiety, such as luminol. In the systems herein, the peroxidase-catalyzed reaction occurs at the higher pH values used for the dehydrogenation or reduction reactions of the substrates and the generation of light from the reaction of the luminescent moiety, the peroxidase, and superoxide anion (O$_2^-$) and/or peroxide.

The resulting assays, which can be performed with horseradish peroxidase or other such peroxidase and with the extraction reagent provided herein, are more stable, appear to be more sensitive and reliable, and are easier to use and automate than assays that use an electron mediator as an intermediate to generate the peroxide. The assays are at least as stable as the shelf life (at least about three months) of any kit provided herein. As a result of the increased sensitivity and reduced number of steps, a single sample can be used in more assays than prior assays. In practice, it has been found that a standard 3 mm blood spot can be used in up to at least about eight assays, compared to a single assay using prior methods.

The assays provided herein also provide a substantial improvement in stability compared to prior assays because NAD(P)$^-$ is provided in the extraction reagent. Extraction reagent, such as trichloroacetic acid (TCA), trifluoroacetic acid (TFA) and 5-sulfosalicylic acid (5-SSA) containing β-nicotinamide adenine dinucleotide, is also provided. In particular, compositions, for extraction of amino acids and sugars from samples, that contain NAD(P)$^+$ and trichloroacetic acid (TCA), trifluoroacetic acid (TFA) and/or 5-sulfosalicylic acid (5-SSA) in an amount effective for extraction of sugars and amino acids are provided.

Kits for performing the luminescence assays herein are also provided. In particular, kits for measuring products or substrates of oxidoreductases that require NAD(P)$^+$/NAD(P)H as cofactors are provided. These kits contain a first reagent containing trichloroacetic acid and NAD(P)$^+$; and a second reagent, containing a peroxidase and an oxidoreductase that catalyzes reactions in which NAD(P)$^+$/NAD(P)H are cofactors, or a second reagent that contains a peroxidase and a third reagent that contains an oxidoreductase that catalyzes reactions in which NAD(P)$^+$/NAD(P)H are cofactors. Kits for the determination of NAD(P)$^+$/NAD(P)H or for determination of an oxidoreductase that requires NAD(P)$^+$/NAD(P)H are also provided. These kits contain a first reagent containing a peroxidase, other than microperoxidase; and a second reagent that contains a substrate of the oxidoreductase or an oxidoreductase that requires NAD(P)$^+$/NAD(P)H. The kits do not include a microperoxidase or an electron carrier that is reduced by NAD(P)H. All kits also include instructions for performing the assays.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, an oxidoreductase is an enzyme that catalyzes a biological oxidation-reduction reaction. Dehydrogenases are oxidoreductases that catalyze dehydrogenation reactions in which hydrogen is transferred from a substrate (or analyte) to NAD(P)$^+$ or in which hydrogen is transferred from NAD(P)H to a substrate (or analyte). The oxidoreductases of interest herein are those in which NAD(P)$^+$/NAD(P)H are cofactors and include dehydrogenases.

As used herein, a serum equivalent is an amount of serum equivalent to the amount of neonate blood that has a hematocrit of 55%.

As used herein, luminescence refers to the detectable EM radiation, generally, UV, IR or visible EM radiation that is produced when the excited product of an exoergic chemical process reverts to its ground state with the emission of light. Chemiluminescence is luminescence that results from a chemical reaction. Bioluminescence is chemiluminescence that results from a chemical reaction using biological molecules as substrates and/or enzymes.

As used herein, a chemiluminescent moiety is a molecule or compound that produces light in a chemical reaction under appropriate conditions.

As used herein, an analyte is any substance that is analyzed or assayed in the reaction of interest. Thus, analytes include the substrates, products and intermediates in the reaction, as well as the enzymes and cofactors.

As used herein, multi-analyte analysis is the ability to measure many analytes in a single specimen or to perform multiple tests from a single specimen.

The Assays

The assays provided herein are based on the discovery that NAD(P)H that is generated in the dehydrogenation or reduction reactions can be used in a peroxidase-catalyzed reaction to produce the superoxide anion (O$_2^-$) (and/or hydrogen peroxide (H$_2$O$_2$)), which is then reacted with a chemiluminescent moiety in a chemiluminescent reaction. As a result, it is not necessary to include an electron mediator to couple dehydrogenase reactions or reactions involving oxidoreductases in which NAD(P)$^+$ is a cofactor to chemiluminescent reactions.

The methods and products herein provide means to:

(1) assay the activity of oxidoreductases and dehydrogenases (see, e.g., Table 1, below) that catalyze reactions that involve the catalyzed oxidation/reduction and the cofactors NADH/NAD$^+$ or NADPH/NADP$^+$;

(2) detect and quantify NAD⁺/NADH and NADP⁺/NADPH; and (3) detect and quantify substrates, intermediates or products of the reactions catalyzed by the oxidoreductases and dehydrogenases or detect and quantify substrates, intermediates or products of reactions that can be linked to reactions catalyzed by the oxidoreductases and dehydrogenases.

Table 1 lists exemplary dehydrogenases and corresponding substrates.

TABLE 1

| Substrate | Dehydrogenase |
| --- | --- |
| D-glucose | glucose dehydrogenase |
| D-glucose-6-phosphate | glucose-6-phosphate dehydrogenase |
| glyceraldehyde-3-phosphate | glyceraldehyde-3-phosphate dehydrogenase |
| lactate | lactate dehydrogenase |
| malate | malate dehydrogenase |
| 3-α-hydroxysteroid | 3-α-hydroxysteroid dehydrogenase |
| L-glutamate | L-glutamate dehydrogenase |
| L-leucine | L-leucine dehydrogenase |
| sarcosine | sarcosine dehydrogenase |
| ethanol | alcohol dehydrogenase |
| L-phenylalanine | L-phenylalanine dehydrogenase |
| D-galactose | D-galactose dehydrogenase |
| amine | amine dehydrogenase |

The products and methods provided here are particularly useful for diagnosis of disease characterized by deficiencies in any substrates, intermediates or products or defects or deficiencies in any of the oxidoreductases and dehydrogenases in which NAD(P)⁺/NAD(P)H are cofactors.

Components of the Assays

Specimens

The assays provided herein are suitable for determination of any substrates, intermediates or products, such as amino acids and sugars, of reactions that are catalyzed by oxidoreductases and dehydrogenases in which NAD(P)⁺/NAD(P)H are cofactors, determination of any of the oxidoreductases and dehydrogenases in which NAD(P)⁺/NAD(P)H are cofactors or for determination of NAD(P)⁺/NAD(P)H in any sample including foods and body fluids or tissues, such as blood, serum, saliva, CSF, hair and urine.

Accordingly, the assays may also be used in methods for diagnosing inborn errors of metabolism and acquired metabolic disorders. The assays are useful for neonatal diagnosis and for prenatal diagnosis using cultured amniocytes, amniotic fluid, chorionic villi or fetal blood. Disorders that can be diagnosed include, but are not limited to: phenylketonuria, maple syrup urine disease, galactosemia, hypersarcosinemia, thymine uraciluria, sulfituria, isovaleric acidemia, saccharopinuria, 4-hydroxybutyric aciduria, glucose-6-phosphate dehydrogenase deficiency, pyruvate dehydrogenase deficiency hyperpipecolic acidemia and hyperprolinemia I.

Substrates and oxidoreductases

Any substrate for which a reaction can be catalyzed by an NAD(P)H requiring dehydrogenase or oxidoreductase or that can be linked via a second (or subsequent) chemical reaction to a reaction catalyzed by an NAD(P)H requiring dehydrogenase or oxidoreductase can be determined by the methods provided herein. The oxidoreductases include, but are not limited to: glucose dehydrogenase, lactate dehydrogenase, glyceraldehyde-3-phosphate dehydrogenase, malate dehydrogenase, 3-α-hydroxysteroid dehydrogenase, L-glutamate dehydrogenase, leucine dehydrogenase, sarcosine dehydrogenase, alcohol dehydrogenase, amine dehydrogenase, galactose dehydrogenase, dihydrouracil dehydrogenase, sulfite dehydrogenase, isovaleryl co-dehydrogenase, saccharopine dehydrogenase, succinate semialdehyde dehydrogenase, glucose-6-phosphate dehydrogenase, pyruvate dehydrogenase, L-picolate dehydrogenase and proline dehydrogenase. The substrates include, but are not limited to, any substrates of the above oxidoreductases, such as galactose, phenylalanine and branched-chain amino acids, such as leucine and isoleucine, or substrates, products or intermediates of the reaction or reactions that produce(s) substrates of the oxidoreductases.

Peroxidases and chemiluminescent moieties

The peroxidases intended for use herein include, but are not limited to: horseradish peroxidase, lactoperoxidase, any haloperoxidase, myeloperoxidase and any other peroxidase that is empirically determined to catalyze the requisite reactions. Suitable concentrations of peroxidase in the resulting reaction may be determined empirically, but typically between about 1 mU and 50 units per test are employed.

The chemiluminescence-generating systems intended for use herein include any that are catalyzed by a peroxidase and require superoxide anion ($O_2^-$) (and/or hydrogen peroxide ($H_2O_2$)). Typical light-generating systems include, but are not limited to, luminol, isoluminol, peroxyoxalate-fluorophore, acridinium ester, acridan, hemin, naphthalene derivatives, such as 7-dimethylamino-naphthalene-1,2-dicarbonic acid hydrazide and cypridina luciferin analogs, including 2-methyl-6-[p-methoxy phenyl]-3,7-dihyroimidazo[1,2-α]pyrazin-3-one, 2-methyl-6-phenyl]-3,7-dihyroimidazo[1,2-α]pyrazin-3-one and 2-methyl-6-[p-[2-[sodium 3-carboxylato-4-(6-hydroxy-3-xanthenon-9-yl]phenylthioureylene]ethyleneoxy]phenyl]-3,7-dihyroimidazo[1,2-α]pyrazin-3-one. The most commonly used chemiluminescent moieties intended for use herein include, but are not limited to, luminol, isoluminol, N-(4-aminobutyl)-N-ethyl isoluminol (ABEI), N-(4-aminobutyl)-N-methyl isoluminol (ABMI), which have the following structures and participate in the following reactions:

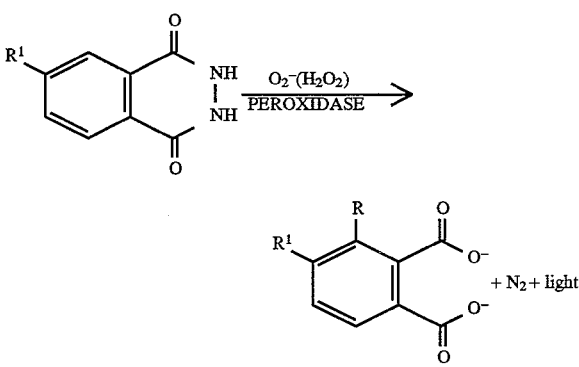

in which luminol is represented, when R is $NH_2$ and $R^1$ is H; isoluminol, when R is H and $R^1$ is $NH_2$; for ABEI ((6-[N-(4-aminobutyl)-N-ethylamino]-2,3-dihyrophthalazine-1-4-dione), when R is H and $R^1$ is $C_2H_5$-N-$(CH_2)_4NH_2$; and for ABMI ((6-[N-(4-aminobutyl)-N-methylamino]-2,3-dihyrophthalazine-1-4-dione), when R is H and $R^1$ is $CH_3$-N-$(CH_2)_4NH_2$.

Applications of the Assays

A. Human diagnostics

The assays herein may be used to detect deficiencies in oxidoreductase activity or substrates, intermediates or products of reactions catalyzed by such enzymes and may thereby be used to diagnose and manage metabolic disorders.

1. Inborn errors of metabolism that can be diagnosed by the assays provided herein Any disease for which a reaction of a substrate, product or intermediated may be catalyzed by an oxidoreductase in which $NAD(P)^+/NAD(P)H$ is cofactor, or coupled to a reaction catalyzed by such oxidoreductase, or that involves a defect in such an oxidoreductase or an alteration in the activity of such oxidoreductase may be diagnosed or indicated by the assays provided herein.

These diseases that can be diagnosed or indicated by the methods herein and the corresponding enzyme that is deficient or defective include, but are not limited to, the following:

TABLE 2

| Disease | Defective or deficient enzyme |
| --- | --- |
| galactosemia: | |
| Type I | galactose-1-phosphate uridyltransferase |
| Type II | galactokinase |
| Type III | epimerase |
| maple syrup urine disease | branched-chain ketoacid decarboxylase |
| phenylketonuria | phenylalanine 4-monooxygenase |
| hypersarcosinemia | sarcosine dehydrogenase |
| thymine uraciluria | dihydrouracil dehydrogenase |
| sulfituria | sulfite dehydrogenase |
| saccharopinuria | saccharopine dehydrogenase |
| 4-hydroxybutyric aciduria | succinate semialdehyde dehydrogenase |
| glucose-6-phosphate dehydrogenase deficiency | glucose-6-phosphate dehydrogenase |
| pyruvate dehydrogenase deficiency | pyruvate dehydrogenase |
| hyperpipecolic acidemia | L-picolate dehydrogenase |
| hyperprolinemia I | proline dehydrogenase |

Each of the substrates set forth in Table 2 may be determined by the methods herein using the corresponding enzyme, if it is a dehydrogenase, or using a dehydrogenase that acts on the substrate (see, e.g., Table 1 ), or by coupling a reaction of the enzyme via $NAD(P)^+/NAD(P)H$ and measuring chemiluminescence as described herein. The concentration of a substrate in a body fluid, if below a certain level, is indicative of the disorder. Diseases that are characterized by alterations in the amounts or types of amino acids present in a body fluid or tissue sample or by an alternation in one of the oxidoreductases that can be determined herein may thereby be diagnosed.

2. Acquired disease that can be diagnosed by the assays provided herein

Numerous diseases can be diagnosed or indicated using the methods herein. The following is a non-limiting sample of such diseases.

(a) Myocardial infarction

Lactate dehydrogenase (LDH) and α-hydroxybutyrate dehydrogenase activities are elevated in myocardial infarction (see, e.g., Kachmar et al. (1976) pp. 652–660 in *Enzymes, in Fundamentals of Clinical Chemistry*, Tietz, ed., Saunders, Philadelphia. For example, LDH oxidizes lactate to pyruvate in the presence of $NAD^+$. The resulting NADH can be measured using the methods herein by coupling the oxidation of lactate to the peroxidase-catalyzed reactions herein. The amount of NADH that is produced is directly proportional to LDH. Thus, lactate dehydrogenase activity or α-hydroxybutyrate activity is used in diagnosing myocardial infarction.

(b) Liver damage

Elevated levels of isocitrate dehydrogenase (ICDH) and sorbitol dehydrogenase occur in hepatocellular damage (see, e.g., Bauer et al. (1970), pages 449–453, in *Bray's Clinical Chemistry*, Tietz, ed., Saunders, Philadelphia). Thus, an assay, of, for example, a blood sample, that determines NADPH in a reaction in which the conversion of L-isocitrate to 2-oxoglutarate in the presence of $NADP^+$ assesses ICDH activity and, thus, is indicative of liver damage. Therefore, liver damage can be detected by determining sorbitol dehydrogenase activity or isocitrate dehydrogenase activity.

(c) Hemolytic anemia

Hemolytic anemia can be detected by determining glucose-6-phosphate dehydrogenase activity in a dehydrogenation reaction of glucose-6-phosphate (see, e.g., Lowe et al. (1972) *Clin. Chem.* 18:440). The amount of NADPH formed is directly proportional to glucose-6-phosphate activity.

(d) Gastric malabsorption disorders

Gastric realabsorption can be detected, for example, by determining mannitol dehydrogenase activity (see, e.g., Lunn et al. (1989) *Clinica Chimica Acta* 183:163). Mannitol dehydrogenase (MDH) activity is measured in a reaction in which the amount of $NAD^+$ is measured in a MDH catalyzed reaction of D-fructose in the presence of NADH according to the methods herein. The amount of $NAD^+$ determined is proportional to MDH activity.

(e) Diabetes mellitus

Diabetes can be determined by measuring glucose using glucose dehydrogenase.

(f) Tumors

The formation and growth of malignancies, such as leukemia, is correlated with high production of highly reactive $O_2$ species, such as $O_2^-$, $^1O_2$, $H_2O_2$ and ·OH (see, e..g., Zimmerman et al. (1993), pages 496–500, in *Proceedings of the VIITh Internatl. Symp. on Bioluminescence and Chemiluminescence*, Banff, Szalay et al., eds., John Wiley and Sons, Chichester; Bierlich et al. 1993), pages 441–445, in *Proceedings of the VIITh Internatl. Symp. on Bioluminescence and Chemiluminescence*, Banff, Szalay et al., eds., John Wiley and Sons, Chichester). Thus, oxidoreductase activity can serve as a diagnostic marker of tumor growth (or reduction during treatment).

B. Human, veterinary and agricultural applications

The methods herein may be used in other diagnostic assays in which a substrate or product of the assay reaction is labeled with an oxidoreductase, cofactor or substrate of an oxidoreductase. These assays include, but are not limited to: (1) ligand binding assays in immunoassays that use oxidoreductase labeled antigens or antibodies (such as the homogeneous enzyme immunoassays, see, e.g., U.S. Pat. Nos. 4,191,613 and 3,875,011); (2) receptor assays that use oxidoreductase-labeled ligands or receptors; (3) protein binding assays that use oxidoreductase-labeled ligands or proteins; and (4) nucleic acid hybridization assays in which an oligonucleotide probe is labeled with an oxidoreductase, $NAD(P)^+$, or with a ligand, such as biotin, that can be labeled with an oxidoreductase, or that reacts with a second molecule, such as avidin or streptavidin, that can be labeled with an oxidoreductase, such as glucose-6-phosphate dehydrogenase (see, e.g., Bronstein et al. (1989) *Anal. Biochem.* 180:95–98).

C. Environmental applications

The assays herein may be used in the determination of heavy metal ions, such as mercuric ion, using mercuric dehydrogenase. Organic compounds, such as formaldehyde, can be determined using an appropriate dehydrogenase, such as formaldehyde dehydrogenase.

D. Pharmaceutical, toxicological, and biotechnical applications

The assays may be used to assess the purity of genetically engineered oxidoreductases and aid in drug design by assessing the activities of oxidoreductase/dehydrogenase substrate or cofactor analogs.

E. Food, beverage, and alcohol analyses applications

The assays may be used to determine alcohol levels in beverages and in body fluids using alcohol dehydrogenase. The assays may be used to determine amino acids or sugars in foods and food supplements or additives, such as aspartame.

Kits and Diagnostic Systems

The assay systems may be provided in kit form that is useful for detecting the enzyme, cofactor, substrate, product, or intermediate in a sample, such as a food, body fluid or tissue. All kits also include instructions for performing the assays.

In particular, kits for measuring products, intermediates or substrates of oxidoreductases that require $NAD(P)^+/NAD(P)H$ as cofactors are provided. These kits contain a first reagent containing trichloroacetic acid and $NAD(P)^+$; and a second reagent, containing a peroxidase and an oxidoreductase that catalyzes reactions in which $NAD(P)^+/NAD(P)H$ are cofactors, or a second reagent that contains a peroxidase and a third reagent that contains an oxidoreductase that catalyzes reactions in which $NAD(P)^+/NAD(P)H$ are cofactors.

The kits include the extraction solution that contains $NAD(P)^+$ in an amount or concentration effective to act as a cofactor in the dehydrogenase/oxidoreductase reactions provided herein. Such concentrations vary depending upon the reaction conditions selected and the instruments used for detection. The concentrations can be as low as the detection limits, currently about $10^{-18}$ mol, of the instrument used. Thus, the concentrations can be between about $10^{-18}$ mol and about 0.1, 1, 10, 50 or 100 mM. Typically such concentrations will be between about 0.1 µM or 1 µM and up to 100 mM, preferably between about 0.02 and 10 mM, more preferably between about 0.02 and 5 mM. The kit also includes the oxidoreductase and a peroxidase, which may be in solution or may be provided as a substantially dry powder, e.g., in lyophilized form. The oxidoreductase and peroxidase may be provided together as a solution or suspension or they may be lyophilized together. The kits may also include the chemiluminescent moiety in powder or liquid form and appropriate standards for generating a standard curve from which the unknown may be determined. The kits may also include suitable ancillary reagents, such as the appropriate buffers, such as TRIS or borate buffer, at a pH appropriate for the reaction, generally alkaline pH, typically between about 7 and about 11.5 (e.g., between about 7 and 9.5 for galactose dehydrogenase-catalyzed reactions and between about 9 and 11.5 for phenylalanine dehydrogenase and leucine dehydrogenase-catalyzed reactions), salts for performing the reactions and reaction stopper, such as a chelating agent, including ethylene diaminetetraacetic acid (EDTA). The kits may also include suitable ancillary supplies, such as microtiter plates and vials.

Other kits for the determination of $NAD(P)^+/NAD(P)H$ or for determination of an oxidoreductase that requires $NAD(P)^+/NAD(P)H$ are also provided. These kits contain a first reagent containing a peroxidase, other than microperoxidase; a second reagent that contains a substrate of the oxidoreductase or an oxidoreductase that requires $NAD(P)^+/NAD(P)H$, and may also include suitable ancillary regents and supplies. These kits do not include a microperoxidase or an electron carrier that is reduced by $NAD(P)H$.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

Practice of the Diagnostic Tests

The diagnostic tests provided herein include assays for substrates, intermediates, and product of oxidoreductase/$NAD(P)^+$-catalyzed reactions, assays for the oxidoreductase activity to detect defects or deficiencies in such enzyme, or assays for $NAD(P)^+/NAD(P)H$, and to detect other biomolecules for which reactions may be coupled to a dehydrogenase catalyzed reaction. In view of the disclosure herein and the knowledge of those of skill in the art with respect to such assays, although reference herein is to measuring dehydrogenase substrates and ascertaining dehydrogenase activity, it is understood that any of the reactants or cofactors in such reactions may be detected or determined according to the methods disclosed herein. Application of the assays for the other purposes, however, will be readily apparent in view of this disclosure.

In using the products and practicing the methods provided herein, a sample, such as blood, saliva, CSF, generally undiluted (if necessary, a dose/response curve can be performed to ensure that the concentration of substrate is in the linear range) or aliquots or serial dilutions of the sample, is extracted with extraction reagent (typically 0.2N trichloroacetic acid (TCA) containing β-nicotinamide adenine dinucleotide (generally between about 0.01 and 100 mM (although the concentration can be as low as the sensitivity of the detection means permits), preferably between about 0.01 and 50 mM, more preferably between 0.01 and 10 mM)). Trifluoroacetic acid (TFA) and 5-sulfosalicylic acid (5-SSA) may be used in place of, or in addition to, TCA. A portion (or portions) of the resulting mixture (about 5–25 µl) is (are) introduced into the well of a microplate or other suitable receptacle, enzyme solution (containing a dehydrogenase (about 1–20 mIU) and a peroxidase (typically about 1–5 units) is added, and the resulting mixture is incubated, generally at room temperature. A suitable chemiluminescent reagent, such as luminol, is added, and luminescence of the resulting mixture is measured using known instruments for such purpose. Calculation from a standard dose-response curve will provide the concentration of the analyte of interest.

For example, when using these assays to assess enzyme activity and measure analyte concentration in a blood sample, such as for neonatal diagnosis, a 3 mm blood spot calibrator (containing about 1.25 µl of serum based on a hematocrit value of 55%) is extracted with the extraction reagent (about 100 µl of the 0.2N TCA containing β-nicotinamide adenine dinucleotide (0.5 mg/ml)). The resulting mixture is incubated at room temperature for about an hour, after which a portion (or portions) of the extract is (are) introduced into a suitable receptacle, such as a microplate well when a plate luminometer is used, or a tube when a tube luminometer is used, enzyme solution, containing the oxidoreductase of interest and a peroxidase, preferably horseradish peroxidase, is added and the resulting mixture is incubated for an appropriate period, typically an hour. A luminescent reagent, such as luminol, is added and chemiluminescence is then measured using a standard instrument, such as a tube luminometer, plate luminometer or an automated flow through system, according to the manufacturers instructions. The amounts of luminescent reagent will vary depending upon the instrument used. For example, about 50–100 μl of luminol solution is injected into a plate luminometer and about 300 μl of luminol solution is injected into a tube luminometer. The resulting output signal is measured and the concentration of the unknown analyte is determined by comparison of the output signal with a standard dose-response curve in order to determine the relative concentration of selected analyte. The analyte or the activity of the selected enzyme can thereby be detected or quantified.

The following examples are included for illustrative purposes only and are not intended to limit the scope of the invention.

EXAMPLE 1

ASSAY FOR GALACTOSE

Materials:

TCA (0.2N) containing $NAD^+$ (0.5 mg/ml; 0.79 mM);

luminol solution (1.13 mM) prepared by dissolving 10 mg luminol in 100 μl 1N NaOH, which is then diluted to 50 ml with 50 mM Tris or borate buffer, pH 8.0; and 3 mM blood spot calibrators on Schleicher & Schuell grade 903 filter paper.

Methods

A 3.0 mm blood spot calibrator was punched out of the filter paper. Trichloroacetic acid (100 μl of 0.2N containing β-nicotinamide adenine dinucleotide (0.5 mg/ml, 0.79 mM)) was added and incubated for one hour at room temperature. Aliquots of the extract (25 μl) were introduced into tubes or microplate wells and 100 μl of galactose dehydrogenase (4 mIU) containing 2.5 units of horseradish peroxidase in 0.2M Tris, pH 8.0, was added to each tube or well. The resulting mixture was incubated for one hour at room temperature. Chemiluminescence was measured in an MGM OPTO-COMP tube luminometer. Luminol solution (300 μl, 1.13 mM) was introduced into each tube. The chemiluminescent output was measured for 0.3 seconds.

| Results | |
|---|---|
| Concentration (mg/dl) | Relative light units (RLU) |
| 0 | 7308 |
| 0.4 | 7438 |
| 2.9 | 45241 |
| 5.7 | 135396 |
| 9.1 | 233548 |
| 14.8 | 312250 |

EXAMPLE 2

ASSAY FOR PHENYLALANINE

Materials

The materials were prepared as in Example 1.

Methods

A 3.0 mm blood spot calibrator was punched into an extraction well. Trichloroacetic acid (100 μl of 0.2N) containing β-nicotinamide adenine dinucleotide (0.5 mg/ml) was added and incubated for one hour at room temperature. Aliquots of the extract (10 μl) were introduced into microplate wells and 100 μl of phenylalanine dehydrogenase (20 mIU) containing 2.5 units of horseradish peroxidase in 0.2M Tris, pH 9.3, was added. The resulting mixtures were incubated for one hour at room temperature, 100 μl of the 1.13 mM luminol solution was introduced and chemiluminescence was measured in a plate luminometer (96P luminometer, Berthold, Germany). The output was measured for 0.3 seconds.

| Results | |
|---|---|
| Concentration (mg/dl) | Relative light units (RLU) |
| 0 | 496 |
| 0.7 | 1241 |
| 1.5 | 1883 |
| 3.3 | 3518 |
| 5.1 | 4961 |
| 8.0 | 7038 |
| 19.3 | 11375 |

EXAMPLE 3

ASSAY FOR BRANCHED-CHAIN AMINO ACIDS

Methods

A 3.0 mm blood spot calibrator was punched into an extraction well. Trichloroacetic acid (100 μl, 0.2N) containing β-nicotinamide adenine dinucleotide (0.5 mg/ml) is added and incubated for one hour at room temperature. Aliquots of the extract 10 μl were introduced into tubes and 100 μl of leucine dehydrogenase (10 mIU) containing 2.5 units of horseradish peroxidase in 0.2N Tris, pH 9.3. The resulting mixture was incubated for one hour at room temperature, 300 μl of 1.13 mM luminol solution was added and chemiluminescence was measured in a tube luminometer, as described above. The output was measured for 0.3 seconds.

| Results | |
|---|---|
| Concentration (mg/dl) | Relative light units (RLU) |
| 1.8 | 642 |
| 2.7 | 776 |
| 4.2 | 1078 |
| 8.0 | 1599 |
| 11.2 | 1992 |
| 14.0 | 2078 |
| 18.8 | 2735 |

Since modifications will be apparent to those of skill in this art, it is intended that this invention be limited only by the scope of the appended claims.

I claim:

1. An assay for quantifying an analytic in a sample, said assay comprising:

providing an oxidoreductase, NAD(P)$^+$/NAD(P)H, a peroxidase and a chemiluminescence generating reagent;

in a first reaction, reducing the NAD(P)$^+$ to NAD(P)H, the first reaction catalyzed by the oxidoreductase;

in a second reaction, transferring electrons from the NAD(P)H produced in the first reaction to an $O_2$ molecule to produce at least one of superoxide anion ($O_2^-$) and hydrogen peroxide ($H_2O_2$), the second reaction catalyzed by the peroxidase, and the second reaction not dependent upon a metal ion or other electron mediator;

in a third reaction, producing a measurable chemiluminescence from the chemiluminescence generating reagent and the at leaanion and hydrogen peroxide produced in the second reaction, the third reaction catalyzed by the peroxidase;

measuring the chemiluminescence produced in the third reaction; and correlating the chemiluminescence measured with the quantity of analyte present in the sample.

2. The assay of claim 1 wherein the sample is extracted using an extraction reagent selected from trichloroacetic acid (TCA), trifluoroacetic acid (TFA) and 5-sulfosalicylic acid (5-SSA).

3. The assay of claim 1 wherein the oxidoreductase comprises a dehydrogenase.

4. The assay of claim 1 wherein the oxidoreductase comprises a dehydrogenase selected from the group consisting of alcohol dehydrogenase, glucose dehydrogenase, galactose dehydrogenase, lactate dehydrogenase, glyceraldehyde-3-phosphate dehydrogenase, malate dehydrogenase, 3-α-hyroxysteroid dehydrogenase, phenylalanine dehydrogenase, L-glutamate dehydrogenase, leucine dehydrogenase, sarcosine dehydrogenase, alcohol dehydrogenase, amine dehydrogenase, dihydrouracil dehydrogenase, sulfilte dehydrogenase, isovaleryl c-dehydrogenase, saccharopine dehydrogenase, succinate semialdehyde dehydrogenase, glucose-6-phosphate dehydrogenase, pyruvate dehydrogenase, L-picolate dehydrogenase, and proline dehydrogenase.

5. The assay of claim 1 wherein the peroxidase is selected from the group consisting of horseradish peroxidase, lactoperoxidase, a haloperoxidase and myeloperoxidase.

6. The assay of claim 1 wherein the chemiluminescent moiety is selected from the group consisting of luminol, isoluminol, peroxyoxalate-fluorophore, acridinium ester, acridan, hemin, 7-dimethylamino-naphthalene-1,2-dicarbonic acid hydrazide, 2-methyl-6-[p-methoxy phenyl]-3,7-dihyroimidazo[1,2-α] pyrazin-3-one, 2-methyl-6-phenyl]-3,7-dihyroimidazo[1,2-α] pyrazin-3-one and 2-methyl-6-[p-[2-[sodium 3-carboxylato-4-[6-hydroxy-3-xanthenon-9-yl] phenylthioureylene]ethyleneoxy]phenyl]-3,7-dihyroimidazo[1,2-α] pyrazin-3-one.

7. The assays of any of claims 1–6 wherein the analyte is the oxidoreductase.

8. The assays of any of claims 1–6 wherein the analyte is a substrate of the first reaction.

9. The assays of any of claims 1–6 wherein the first reaction comprises a substrate selected from the group consisting of glucose, glucose-6-phosphate, glyceraldehyde 3-phosphate, malate, 3-α-hydroxysteroid, lactate, L-glutamate, sarcosine, ethanol, homogentisic acid, galactose, branched-chain amino acids, phenylalanine and D-fructose.

10. The assays of any of claims 1–6 wherein the analyte is an intermediate of the first reaction.

11. The assay of any of claims 1–6 wherein the analyte is a product of the first reaction.

12. The assay of any of claims 1–6 wherein the assay is an assay for diagnosis of a metabolic disease.

13. The assay of any of claims 1–6 wherein the assay is an assay for diagnosis of a metabolic disease selected from the group consisting of galactosemia, maple syrup urine disease, phenylketonuria, hypersarcosinemia, thymine uraciluria, sulfinuria, isovaleric acidemia, saccharopinuria, 4-hydroxybutyric aciduria, glucose-6-phosphate dehydrogenase deficiency, and pyruvate dehydrogenase deficiency.

14. The assays of any of claims 1–6 wherein the analyte is a participant in the first reaction, and the assay is an assay for diagnosis of a metabolic disease.

15. The assays of any of claims 1–6 wherein the analyte is a participant in the first reaction, and the assay is an assay for diagnosis of a metabolic disease selected from the group consisting of galactosemia, maple syrup urine disease, phenylketonuria, hypersarcosinemia, thymine uraciluria, sulfinuria, isovaleric acidemia, saccharopinuria, 4-hydroxybutyric aciduria, glucose-6-phosphate dehydrogenase deficiency, and pyruvate dehydrogenase deficiency.

* * * * *